(12) United States Patent
Herrmann

(10) Patent No.: US 10,981,006 B2
(45) Date of Patent: Apr. 20, 2021

(54) HEARING PROSTHESIS EMITTING ULTRASONIC PULSES

(71) Applicant: AUDISENSE GmbH, Luebeck (DE)

(72) Inventor: Vera Herrmann, Luebeck (DE)

(73) Assignee: AUDISENSE GMBH, Luebeck (DE)

( * ) Notice: Subject to any disclaimer, the term of this patent is extended or adjusted under 35 U.S.C. 154(b) by 0 days.

(21) Appl. No.: 15/565,769

(22) PCT Filed: Apr. 27, 2016

(86) PCT No.: PCT/EP2016/059364
§ 371 (c)(1),
(2) Date: Oct. 11, 2017

(87) PCT Pub. No.: WO2016/174065
PCT Pub. Date: Nov. 3, 2016

(65) Prior Publication Data
US 2018/0117328 A1    May 3, 2018

(30) Foreign Application Priority Data
Apr. 28, 2015  (DE) .......................... 102015106560.6

(51) Int. Cl.
*A61N 1/36* (2006.01)
*H04R 25/00* (2006.01)

(52) U.S. Cl.
CPC ..... *A61N 1/36038* (2017.08); *A61N 1/36036* (2017.08); *H04R 25/405* (2013.01); *H04R 25/606* (2013.01); *H04R 2225/67* (2013.01)

(58) Field of Classification Search
CPC .......................... B06B 1/0207; H04R 2225/43
USPC .................................................. 381/315, 317
See application file for complete search history.

(56) References Cited

U.S. PATENT DOCUMENTS

| | | | |
|---|---|---|---|
| 6,394,969 B1 | 5/2002 | Lenhardt | |
| 6,631,197 B1 | 10/2003 | Taenzer | |
| 2004/0196998 A1 | 10/2004 | Noble | |
| 2005/0201574 A1* | 9/2005 | Lenhardt | A61H 23/0245 381/151 |
| 2010/0040249 A1* | 2/2010 | Lenhardt | H04R 25/502 381/316 |
| 2010/0198282 A1* | 8/2010 | Rogers | A61F 7/007 607/3 |
| 2010/0298744 A1* | 11/2010 | Altshuler | A61N 7/02 601/3 |
| 2011/0144719 A1* | 6/2011 | Perkins | H04B 10/1141 607/57 |
| 2012/0008812 A1* | 1/2012 | Sporer | H04R 1/26 381/335 |
| 2014/0355800 A1* | 12/2014 | Kang | H04R 25/00 381/315 |

(Continued)

*Primary Examiner* — Alexander Krzystan
(74) *Attorney, Agent, or Firm* — Andrew Wilford

(57) ABSTRACT

The invention relates to a hearing prosthesis having at least one acoustic converter for converting acoustic signals into electrical signals, and comprising an ultrasound device by means of which a multiplicity of focused, pulsed ultrasonic beams can be generated, wherein the ultrasound device can be fixed in the outer ear and/or outside the ear, and wherein, on the basis of electrical signals generated by the acoustic converter, the ultrasonic beams can be focused on to various physically distributed points in a region of the inner ear or in a region of the auditory pathway in the brain, while stimulating nerves.

14 Claims, 3 Drawing Sheets

(56) References Cited

U.S. PATENT DOCUMENTS

2015/0139439 A1\* 5/2015 Norris .................... H04R 1/323
381/77

\* cited by examiner

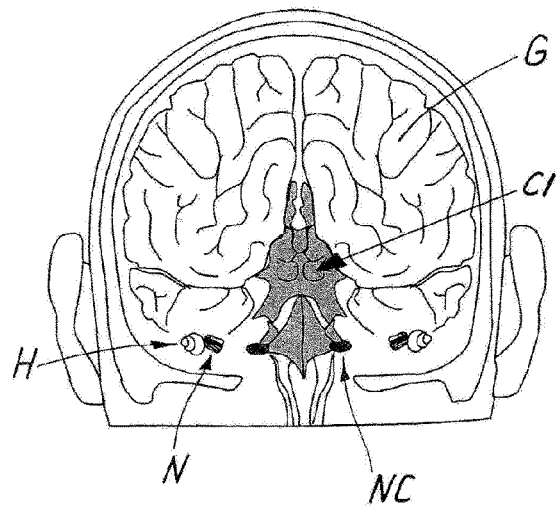
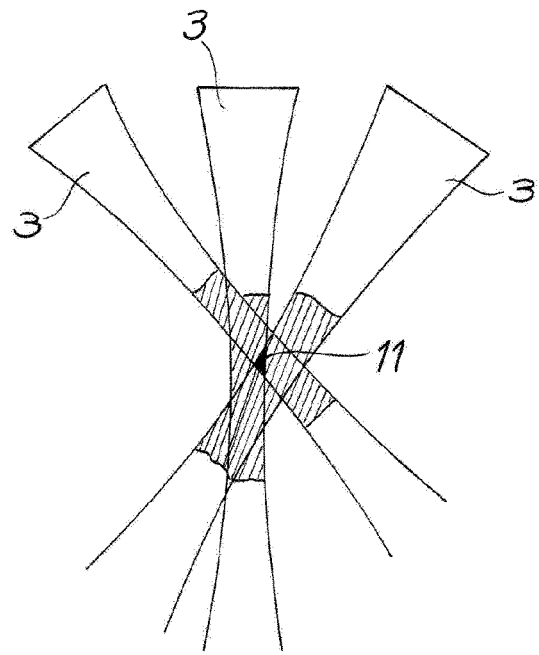
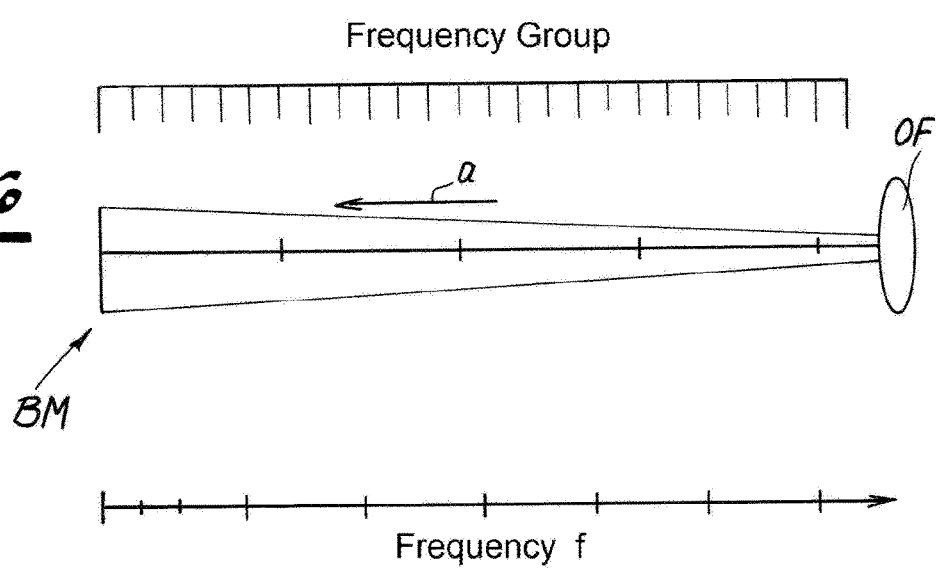

HEARING PROSTHESIS EMITTING ULTRASONIC PULSES

CROSS REFERENCE TO RELATED APPLICATIONS

This application is the US-national stage of PCT application PCT/EP2016/059364 filed 27 Apr. 2016 and claiming the priority of German patent application 102015106560.6 itself filed 28 Apr. 2015.

FIELD OF THE INVENTION

The invention relates to a hearing prosthesis and a method of compensating for hearing loss or auditory defects using such a hearing prosthesis.

BACKGROUND OF THE INVENTION

Against the background of the very large portion of the population with hearing problems, and in view of the severe impairment of those stricken with them, an especially high level of interest exists in auditory prostheses and hearing aids. When hearing is intact, the auricle collects the sound waves from the environment and conducts them through the auditory canal to the tympanic membrane that then vibrates. These vibrations are transmitted via the middle ear to a liquid in the inner ear, more particularly in the cochlea. As a result of the movement of the liquid, fine hair cells within the cochlea are deflected, thereby triggering (bioelectrical) nerve impulses that are forwarded via the auditory nerve to the brain where auditory perception occurs.

Conventional hearing aids work electroacoustically and consequently with acoustic amplification. However, this principle no longer functions if bioelectrical signals can no longer be generated in the cochlea.

In such cases, so-called cochlear implants can possibly be of help. These first convert sound into electrical impulses, and those stimulate the nerves in the inner ear and the auditory nerve by electrodes implanted directly into the cochlea. Speech and noises can thus be perceived again. The functional principle of such cochlear implants is based on the so-called "tonotopy" of the cochlea. In the cochlea, mechanical vibrations coming in from the outside are converted into neural impulses, specifically in such a way as to be ordered anatomically by frequency. Different spatially distributed regions within the cochlea are responsible for the perception of different frequencies, with high frequencies being processed at the outer end and low frequencies being processed at the inner end. In the auditory pathway in the ear, this anatomical sorting by frequency is retained in different regions of the brain. Consequently, the system of the hair cells is set up in the cochlea in such a way that every audible frequency has its specific place of maximum sensitivity. As a result, a certain frequency is associated with each place on the so-called basilar membrane. A "frequency-place mapping" thus takes place in the cochlea that is also referred to as tonotopy. This functionality of the cochlea is exploited in cochlear implants; to wit, using the electrodes that are spatially distributed in the cochlea, electrical impulses that represent a defined audio frequency can be generated in a targeted manner. One drawback here is that such auditory prostheses must be invasively integrated into the cochlea as an implant. This is complex and represents a burden for the patient. Corrections cannot be readily made. Apart from that, due to the conductivity of the tissue surrounding the implant, several nerves are unintentionally stimulated by the electrical impulses that are responsible for hearing different frequencies. This results in a pronounced reduction in the selectivity of the hearing that is to be produced within the cochlea.

Alternatively, modified cochlear implants have therefore already been proposed that are based on the principle of light stimulation and optogenetic activation. In that case, an array of laser diodes is implanted into the cochlea instead of the electrodes. The desired place (on the auditory nerve) can be stimulated in a very targeted manner with the aid of the laser beams. The selectivity of hearing is thereby increased substantially compared to conventional cochlear implants. However, in order to enable the nerve cells of the cochlea to be activated by light, the nerve cells must first be artificially sensitized to light. All of these measures are very elaborate and also only possible by invasive means.

Where such cochlear implants cannot be used due to the severity of the damage to the auditory system, auditory brainstem implants (ABI) can be optionally used. The principle corresponds to that of the cochlear implants, but it is not regions within the cochlea that are stimulated using electrodes, but a step further in the auditory pathway at the cochlear nucleus. Such systems can be used when the cochlea or even the auditory nerve are damaged or even have to be removed, for example as a result of disease. However, the use of auditory brainstem implants is possible only through highly specialized measures. In principle, the need therefore exists among patients in whom classic cochlear implants do not work for approaches that involve other locations of the auditory pathway. Consideration has also been given to performing electrical stimulation on the cochlear nucleus in the brainstem or at the inferior colliculus. Elaborate invasive measures would still be necessary.

A great need therefore exists for a hearing prosthesis that can be used in an extremely wide variety of types of hearing loss or hearing impairment(s) without operative measures and thus noninvasively.

OBJECT OF THE INVENTION

It is therefore the object of the invention to provide such a hearing prosthesis.

SUMMARY OF THE INVENTION

To attain this object, the invention teaches a hearing prosthesis with at least one acoustic converter (for example microphone) for converting acoustic signals into electrical signals and an ultrasound device with which a plurality of focused (or dynamically focusable) pulsed ultrasonic beams can be generated, wherein the ultrasound device is fastenable in the outer ear and/or outside of the ear (of a human body), and the ultrasonic beams are (dynamically) focusable (transcranially) on different spatially distributed points in a region of the inner ear or in a region of the auditory pathway in the brain as a function of the electrical signals generated by the acoustic converter, thereby stimulating nerves.

The invention thus proposes a noninvasive ultrasonic exo-hearing prosthesis. The invention proceeds in this regard from the inherently known insight that hearing loss can be compensated for even in the event of damage to the cochlea if a spatially selective stimulation of the nerve cells is performed in the cochlea or also in other regions of the auditory pathway. However, while stimulation is performed directly in conventional cochlear implants using electrical or optical impulses, the nerves or nerve cells are stimulated according to the invention with focused ultrasonic radiation. At the same time, the tonotopy of the cochlea is exploited in a manner similar to conventional cochlear implants. Specifically, a plurality of focused ultrasonic beams are used to exploit the special anatomical characteristics through targeted stimulation of spatially distributed regions or nerves that represent different audio frequencies. The natural path of the sound is circumvented completely. Unlike cochlear implants, however, the auditory prostheses according to the invention can be placed and fastened in the outer ear or even outside of the (human) ear. The nerve cells that are responsible for the different frequency ranges are stimulated transcranially using focused ultrasonic radiation.

In this regard, the invention proceeds from the insight that nerve and muscle fibers can be stimulated by (focused) ultrasound. This has been established in the past by a multitude of experiments. At high energy levels ($>1$ W/cm$^2$), ultrasound causes neural activities and also has thermal effects. The present considerations are focused only on neural stimulation that can be achieved with the aid of pulsed low-frequency ultrasonic radiation of low intensity. Consequently, the effect is limited to mechanical bioeffects without thermal effects and particularly without tissue damage. The fact that nerve cells and particularly also an auditory nerve of a living thing can be stimulated with the aid of pulsed ultrasonic radiation has been widely demonstrated experimentally (see Leonid R. Gavrilov et al.: *A Study of Reception with the Use of Focused Ultrasound*, Brain Research, 135 (1977) 279-285, and Vincent Colucci et al: *Focused Ultrasound Effects on Nerve Action Potential in Vitro*, Ultrasound in Med. & Biol., Vol. 35, No. 10, 1737-1747, 2009, and Yusuf Tufail: *Transcranial Pulsed Ultrasound Stimulates Intact Brain Circuits*, Neuron 66, 681-694, 2010).

Ultrasonic pulses having a pulse length from 0.01 ms to 1 ms, preferably from 0.05 ms to 0.5 ms are preferably used, with the ultrasonic frequency being preferably less than 1000 kHz, more preferably less than 700 kHz, for example 100 to 900 kHz, and especially preferably 250 to 700 kHz. It is possible for all of the beams to have the same frequency. The individual ultrasonic pulses can each have a pulse power of 0.01 to 0.1 W/cm$^2$, i.e., 10 mW/cm$^2$ to 100 mW/cm$^2$. In the described frequency range, an optimal relationship can be achieved between transcranial transmission on the one hand and the absorption of the ultrasonic radiation in the nerve cells on the other hand. The ultrasonic stimulation/stimulating ultrasonic pulse must be capable of successfully performing the stimulation repeatedly in real time based on a time line of the action potential and the latency period of the auditory nerve according to acoustic need. The above-described pulse length is advantageous because stimulation of longer duration can lead to blocking of the auditory nerve. However, such stimulation pulses can also be used according to the invention to compensate for tinnitus by blocking the auditory nerve.

Consequently, a medical device is provided according to the invention that can compensate noninvasively for hearing loss ranging from amblyacousia to complete deafness by focused, pulsed ultrasound and can alternatively also "compensate" for tinnitus. Another important aspect here is that patients in whom hearing loss could, in principle, be compensated for with a cochlear implant often have no auditory experience of any kind. This fact makes any testing of the cochlear implant difficult from the very outset in terms of psychoacoustics. In contrast, with the noninvasive ultrasonic exo-hearing prosthesis according to the invention, it is possible to simulate such psychoacoustic effects through testing with people with intact hearing, for example in a soundproof room, and correctly reproduce them in the speech processor of the hearing prosthesis. Multichannel sound analysis with simultaneous multichannel sound generation in the auditory pathway is possible, just as would be performed by an intact ear. The exo-hearing prosthesis according to the invention can thus be used not only without an operation, but it can also be adapted optimally and individually to the degree of hearing loss. The frequency selectivity corresponds to healthy hearing and, in particular, spatial hearing is also enabled. It is especially advantageous that such an exo-hearing prosthesis can be interchanged and used in an age-dependent manner and thus in different generations.

According to the invention, generating a plurality of (dynamically) focused ultrasonic beams to achieve the spatially selective stimulation of the desired regions, for example in the cochlea or on the auditory nerve, is of particular importance. To this end, the ultrasound device can have, beside an ultrasonic driver, at least one ultrasound array with which a plurality of dynamically focusable ultrasonic beams can be generated, all of which preferably have the same ultrasonic frequency. The dynamic focusing of ultrasonic beams or ultrasonic waves is commonly performed in medical diagnostics with the aid of ultrasound arrays. The elements of the ultrasound array are divided up into several groups, so that the ultrasound device can be preferably used to generate more than 10, especially preferably more than 20 dynamically focusable and deflectable ultrasonic beams. The number of groups is established in consideration of the realistic frequency selectivity; for example, 20 to 30 groups are provided. This number of groups of array elements then corresponds to the number of frequency groups in the cochlea, for example. The individual array elements of a group are arranged in an array so as to be spatially distributed. The energy of an "individual beam" from a single element is relatively small, particularly when considering the absorption in the tissue. The pulse energy reaches the desired level in order to perform the required stimulation only in a small, finely adjustable focus of the beams of a group on a defined position within the cochlea (or also on the auditory nerve). Consequently, each group of array elements is responsible for stimulating a defined region of the nerve fibers.

The dynamic focusing and hence continuous adjustment of the focal position is advantageous. It is true that the ultrasound array has a rigid construction, so that each element and also each group has a fixed position (relative to one another). However, no absolute fixation of the ultrasound device or of the array on the skin or in the outer ear is possible in practice. Since the position of the ultrasound device and array can thus change, appropriate correction is required. For this purpose, the invention proposes in an especially preferred development that one or more reference beams be produced with the ultrasound source that are focused on one or more reference points independently of the signals generated with the acoustic converter (for example reference points in or on the cochlea). The position of the ultrasound device, for example of the ultrasound array, is thus checked continuously during operation by one or more reference beams, for example through scanning of the tip of the cochlea. Over the course of a "startup," information regarding the position, size, and orientation of the cochlea is first identified by a (three-dimensional) ultrasonic scan of the entire cochlea. The "target points" for the spatially selective stimulation with the individual ultrasonic beams are then established on that basis. If altered distances and angles of incidence are identified by a control program with the aid of the reference beams, the focal depths and the angles of incidence of the individual groups relative to the reference beam or the reference beams are corrected in real time.

In addition to the acoustic converter (microphone) and the ultrasound array/ultrasonic driver, the hearing aid also has an analog-to-digital converter, a speech processor, and/or an encoder, for example. Moreover, a power supply is provided.

The control program that calculates and controls the ultrasonic beams (for example angle, focus, etc.) and also performs the calculated corrections, is stored in the hearing aid.

The object of the invention is also a method of compensating for hearing loss or auditory defects with such a hearing prosthesis, and to a method of operating and/or using/employing such a hearing prosthesis, with the hearing prosthesis being fastened in the outer ear and/or outside of the ear, and with the ultrasonic beams being focused (transcranially) on different spatially distributed points in a region of the inner ear or in a region of the auditory pathway in the brain as a function of the electrical signals generated by the acoustic converter, thereby stimulating different spatially distributed regions (of nerves) in the cochlea or in a region of the auditory pathway that represent different audio frequencies.

As described above, stimulation of the nerves can occur within the cochlea. Other sites of stimulation are also possible, however, for example, directly on the auditory nerve, or stimulation of the cochlear nucleus and of the inferior colliculus. Corresponding positions can be identified by means or MRT, for example. Corrections can be performed with the aid of reference beams for these stimulation sides as well. The reference beams can, in turn, be fixed on the tip of the cochlea, or at another fixing point in the cranium.

As described above, in order to generate a plurality of dynamically focusable ultrasonic beams, an ultrasound array is used whose array elements are divided up and combined into groups, each of which represents an acoustic frequency range, with stimulation occurring at one point through superimposition of the beams of the individual elements incident at different angles. At least one reference beam can be focused on at least one reference point independently of the signals generated with the acoustic converter, and the position of the foci of the remaining ultrasonic beams can be corrected dynamically in real time on the basis of the reference beam.

The focusing of the ultrasonic beams has special significance according to the invention. This is done in the described manner with the aid of ultrasound arrays, for example. This method can be further optimized by using not only focused ultrasound to stimulate a defined region of the nerve cells, but at least two ultrasonic beams generated at a spacing from one another that are focused on a common point. The individual focal volumes are laterally narrow but can be optionally relative long axially. Through the use of ultrasound arrays, for example, it is possible to achieve a focal volume of reduced size through superposition of several (at least two) ultrasonic fields. The superimposition results in a reduction of the focal volume in which the ultrasonic level required for stimulation is reached. Such an arrangement is very favorable, since the ultrasound does not cause any stress or any additional reactions in the surrounding tissue in this way. For instance, noise resulting from unwanted stimulation or inhibition of nearby nerve fibers is prevented.

It is true that the use of ultrasonic radiation in conjunction with hearing aids or auditory prostheses is already known. The ultrasonic frequency is used as a carrier frequency for audio signals, so that signals induced by ultrasound, for example, are transmitted via skin vibrations to the region of the auditory system or of the brain, where they can be decoded (for example, see U.S. Pat. No. 6,631,197, US 2004/0196998, WO 2000/021440 [U.S. Pat. No. 6,394,969], and WO 2005/072168 [US 2005/0201574], as well as US 2014/0355800). This is in contrast to the direct spatially selected stimulation of nerves with focused beams that stands in the foreground of the invention, with the ultrasonic waves that are used preferably having the same frequency.

BRIEF DESCRIPTION OF THE DRAWING

The invention is described in further detail below with reference to a schematic drawing that illustrates only one exemplary embodiment and in which:

FIG. 5 is a simplified, schematic view of additional areas of application of the hearing prosthesis according to the invention;

FIG. 6 is a graph of the tonotopy of the cochlea; and

FIG. 7 shows the superposition of several ultrasonic beams in an embodiment according for example to FIG. 1.

SPECIFIC DESCRIPTION OF THE INVENTION

Figure 1:
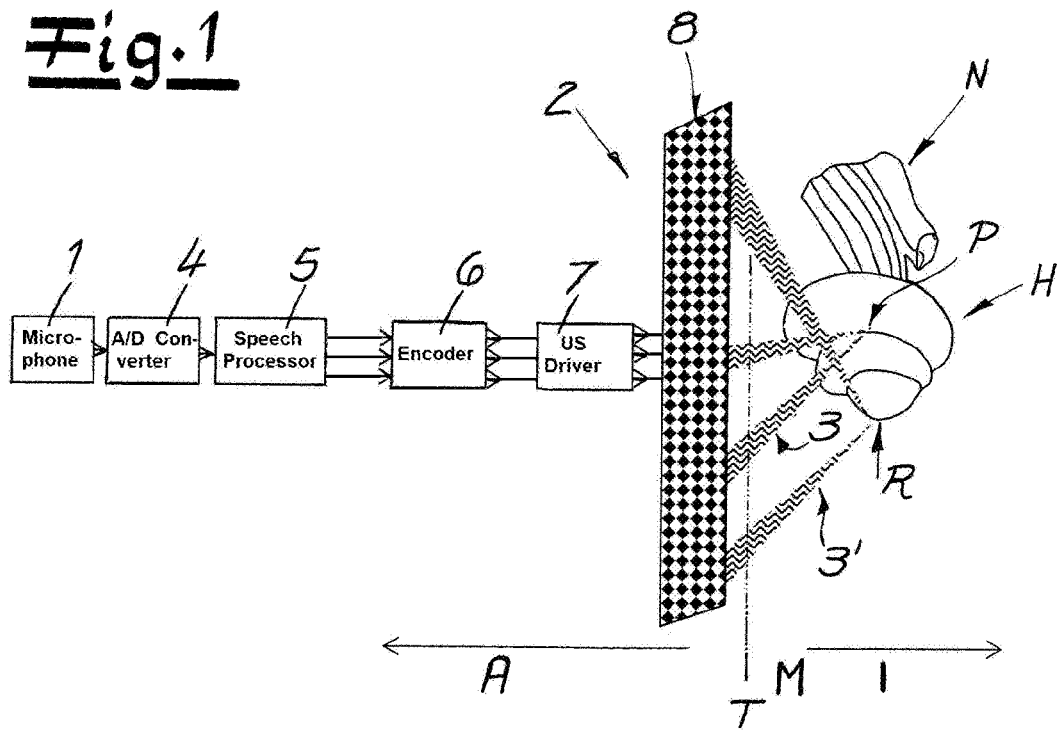
FIG. 1 is a highly schematic view of a hearing prosthesis according to the invention.

The drawing shows an exo-hearing prosthesis according to the invention for compensating for hearing loss or auditory defects. This hearing prosthesis has at least one acoustic converter 1 (for example a microphone for converting acoustic signals into electrical signals). Moreover, the hearing prosthesis has at least one ultrasound device 2 with which a plurality of focused, pulsed ultrasonic beams are generated. This ultrasound device is fastened in the outer ear A or outside of the ear. The ultrasonic beams 3 are dynamically focused transcranially on different spatially distributed points P (behind the tympanic membrane T and behind the middle ear M) in a region of the inner ear I or in a region of the auditory pathway in the brain G as a function of the electrical signals generated by the acoustic converter 1, thereby stimulating nerves.

The hearing prosthesis according to the invention is based on the correlation illustrated in FIG. 6 between a spatial arrangement of the "rolled-out basilar membrane" and the corresponding frequency. In a healthy ear, the acoustic waves that are received from the outside are transmitted via the tympanic membrane to the inner ear I and thus to the cochlea H. The fluid in the cochlea H then deflects the basilar membrane BM that divides the cochlea H into two chambers. A direction of propagation a of the traveling wave on the basilar membrane and the oval-shaped window OF are shown. Movement of the basilar membrane results in movement of hair cells, with the array of hair cells being anatomically such that every audible acoustic frequency has its specific location of maximum sensitivity. This is shown in FIG. 6. This frequency map is also referred to as the tonotopy of the cochlea H. Conventional cochlear implants also take advantage of this principle by using electrodes to electrically stimulate regions distributed spatially there.

According to the invention, the different regions are now stimulated with the aid of focused ultrasonic radiation 3. According to FIG. 1, acoustic waves are converted by a microphone 1 into electrical impulses and transmitted via an analog-to-digital converter 4 to a speech processor 5 that processes these signals. The frequency- and time-resolved amplitudes of the ultrasonic beams are encoded on multiple channels, so that multichannel control signals for an ultrasonic driver 7 of an ultrasound device 2 are generated. With the aid of these control signals, the ultrasound device 2 generates a plurality of ultrasonic beams 3 that are thus focused on different spatially distributed points P in a region of the inner ear I or in a region of the auditory pathway in the brain G as a function of the electrical signals generated by the acoustic converter 1, so that different spatially distributed regions of nerves in the cochlea or in a region of the auditory pathway are stimulated that represent different audio frequencies (according to FIG. 6).

FIGS. 1 to 4 show embodiments in which nerve cells in the cochlea H are stimulated with the aid of ultrasonic beams 3. Each individual ultrasonic beam 3 is focused to a defined depth by corresponding control signals with a defined angle of incidence.

In this embodiment, the ultrasound device 2 has for this purpose an ultrasound array 8 that generates a plurality of dynamically focusable ultrasonic beams 3. The array has a plurality of array elements that are grouped together into respective groups, with each group representing a defined audio frequency range. For instance, in order to achieve a realistic frequency selectivity, it can be advantageous to provide 25 groups of array elements to generate 25 focused ultrasonic beams (for example at the same ultrasonic frequency). The number of groups of array elements thus corresponds to the number of frequency groups in the cochlea. Each group is thus responsible for a defined region of the nerve fibers. The control signals generate the ultrasonic radiation 3 by stimulating certain elements or groups of the array. The duration of the irradiation and the repetition of the stimulation/blocking that is produced is generated in the ultrasonic driver 7 for each individual element or for the group of arrays by the encoded control signals from the speech processor 5. The combination of the active elements/groups is generated in real time according to the incident radiant energy of the ultrasound 3 and the psychoacoustic requirements of realistic auditory perception.

Figure 2:
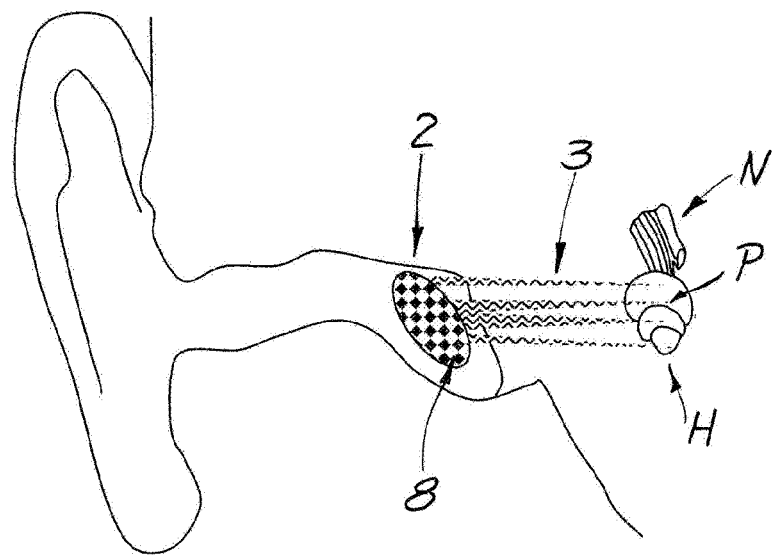
FIG. 2 shows the hearing prosthesis according to FIG. when positioned in the outer ear.

FIG. 2 for example shows that the individual ultrasonic beams 3 are directed into different regions of the cochlea H. It is also advantageous if one or more reference beams 3' are generated using the ultrasound source 2 that are focused on one or more reference points R as a function of the signals generated in the acoustic converter 1. This is shown in FIG. 1. Two reference beams 3' can be seen in that figure that are focused on the tip of the cochlea H as a fixing point, for example. If the position of the hearing aid or of the ultrasound device 2 changes during use, this is detected with the aid of the reference beams 3', and a correction of the other ultrasonic beams 3 can be performed in real time. The position of the ultrasound device 2 is thus checked continuously during use by one or even two reference beams 3' by scanning for the tip of the cochlea H. The focal depths and the angle of incidence of the other ultrasonic beams 3 are then corrected relative to the reference beam 3' in real time. FIG. 1 also shows that two (or also more) ultrasonic beams 3 generated at a spacing from one another can be focused on a point P, so that a reduced focal volume is then produced by superposition of the beams. This is illustrated in enlarged form in FIG. 7 using the example of three superposed, focused beams 3. This superposition takes into account the fact that the individual focal volumes can be optionally narrow laterally but quite long axially. the superposition of several ultrasonic fields 3 serves to form a focus 11 with a reduced focal volume (see FIG. 7). Such an approach also offers the advantage that stress caused by the ultrasonic radiation in the tissue is low, since the required stimulation energy is reached only at the focus in the cochlea.

FIG. 2 shows a first embodiment in which an exo-hearing prosthesis is positioned in the outer ear A. This positioning is advantageous if the patient is completely deaf, for example.

Figure 3:
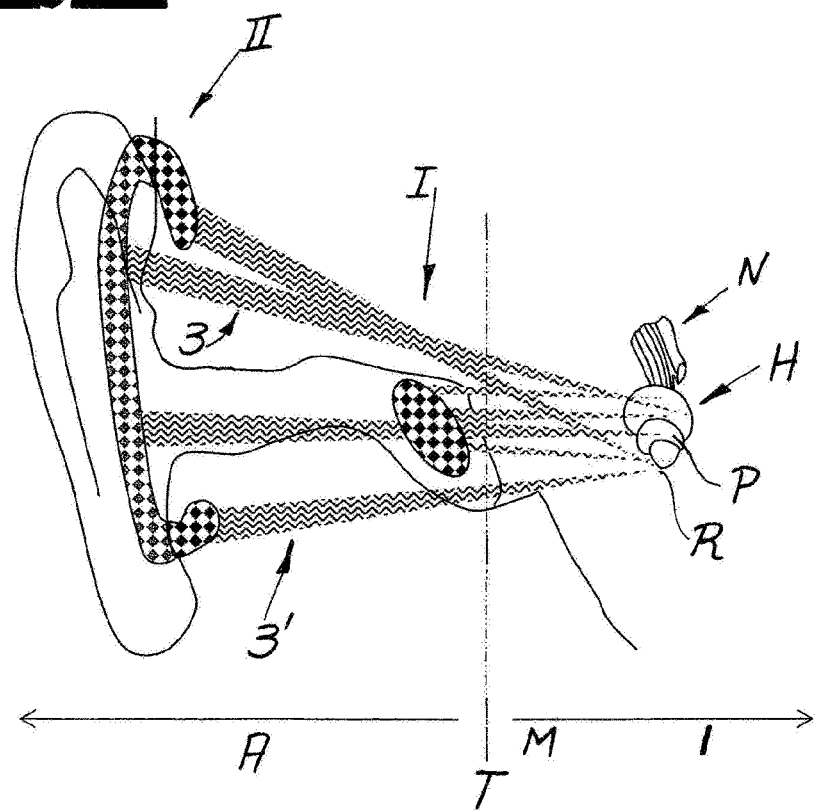
FIG. 3 shows the prosthesis of as in FIG. 2 when positioned outside the ear.

In contrast, position I of FIG. 3 shows this embodiment according to FIG. 2 on the one hand and, for comparison, position II shows an embodiment with an exo-hearing prosthesis that is fastened outside of the ear on the other hand. This positioning II can be advantageous for amblyacousia or even tinnitus. Positioning is noninvasive in all cases, however.

Figure 4:
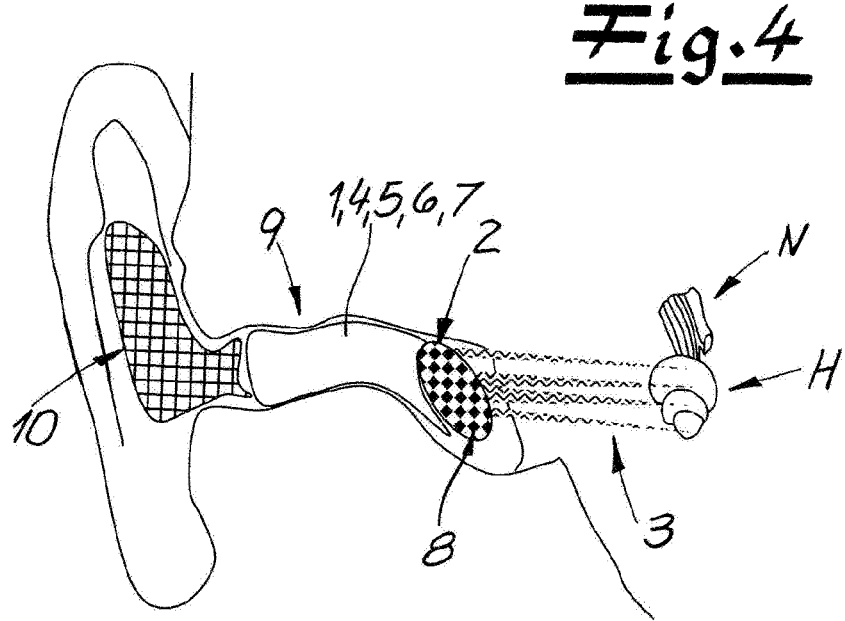
FIG. 4 shows another prosthesis like that of FIG. 1.

FIG. 4 shows an embodiment according to FIG. 2, but also with an electronic controller 9 and a power supply 10 that is optionally constituted by solar cells in the illustrated embodiment. The electronic controller 9 has the microphone 1, the analog-to-digital converter 4, the speech processor 5, the encoder 6, and the ultrasonic driver 7. The ultrasound array 8 is also shown. However, the invention also includes embodiments in which another power supply such as a battery, accumulator, or the like can be provided.

FIGS. 1 to 4 show embodiments in which the stimulation of nerve cells in the cochlea H is achieved using ultrasonic radiation.

Alternative possibilities for stimulation are shown in FIG. 5. The region of the cochlea H is immediately visible. Alternatively, however, the auditory nerve N can also be stimulated with ultrasonic radiation, particularly if the cochlea H has been damaged by disease to the point that stimulation is no longer possible in the cochlea H, for example. If the auditory nerve N is also damaged or has had to be removed due to disease, another development of the invention offers the possibility of stimulating other regions of the auditory pathway in the brain G, such as the cochlear nucleus NC or also the inferior colliculus CI, for example. In this regard, the invention makes use of the fact that the tonotopy (frequency-place map) of the cochlea H continues into the brain in the form of a ribbon. Consequently, there are regions there in which a defined frequency is associated with each location, so that the spatially selective stimulation of nerve cells is also possible in these regions of the brain—for example, when it is no longer possible to stimulate the auditory nerve. However, this conversion is also performed in a noninvasive manner.

The invention claimed is:
1. A hearing prosthesis, comprising:
   a speech processor for converting acoustic speech signals into a plurality of separate neither amplitude nor frequency modulated electrical signals each representing presence of sound within a respective frequency range of the acoustic speech signals; and
   an ultrasound device fastenable in or outside an ear for receiving the plurality of electrical signals,
      generating respective focusable, pulsed and unmodulated ultrasonic beams each representing a respective one of the electrical signals, and focusing each of the ultrasonic beams on respective different spatially distributed points in a region of the inner ear or in a region of the auditory pathway in the brain as a function of the frequencies corresponding to the electrical signals generated by the acoustic converter, thereby stimulating nerves.

2. The hearing prosthesis defined in claim 1, wherein the ultrasound device has at least one ultrasound array with which the focusable ultrasonic beams are generated.

3. The hearing prosthesis defined in claim 1, wherein more than 10 of the ultrasonic beams are generated by the ultrasound device.

4. The hearing prosthesis defined in claim 1, wherein a pulse length of the ultrasonic beams is 0.01 ms to 1 ms.

5. The hearing prosthesis defined in claim 4, wherein a frequency of each of the ultrasonic beams is less than 1000 kHz.

6. The hearing prosthesis defined in claim 4, wherein the ultrasonic beams each have a pulse power of 0.01 to 0.1 W/cm$^2$.

7. The hearing prosthesis defined in claim 1, further comprising the step of:
    generating one or more reference ultrasonic beams with the ultrasound source; and
    focusing the reference beams on one or more respective reference points as a function of the signals generated in the acoustic converter.

8. A method of compensating for hearing loss or auditory defects, the method comprising the steps of:
    providing using a hearing prosthesis having at least one acoustic converter for converting acoustic signals into a plurality of separate pulsed electrical signals each representing a respective frequency range of the acoustic signals;
    receiving with an ultrasound device the plurality of electrical signals;
    generating with the ultrasound device from the electrical signals a plurality of amplitude and frequency unmodulated ultrasonic beams each representing sound in a respective one of the frequency ranges of the acoustic signals;
    fastening the hearing prosthesis in or outside an ear; and
    focusing the ultrasonic beams on respective different spatially distributed points in a region of an inner ear of the ear or in a region of an auditory pathway in the brain as a function of the electrical signals generated by the acoustic converter, thereby stimulating different spatially distributed regions in the cochlea or in a region of the auditory pathway that represent different audio frequencies.

9. The method defined in claim 8, wherein the individual ultrasonic beams are focused on different spatially distributed points within the cochlea or auditory nerve or cochlear nucleus or inferior colliculus.

10. The method defined in claim 8, wherein, in order to generate the plurality of ultrasonic beams, an ultrasound array is used whose array elements are divided up and combined into groups that each represent an acoustic frequency range.

11. The method defined in claim 8, wherein at least two ultrasonic beams are generated spaced from one another, focused on a point, and superposed, thereby producing a reduced focal volume.

12. The method defined in claim 8, further comprising the step of:
    focusing at least one reference beam on at least one reference point independently of the signals generated with the acoustic converter, and
    correcting a position of foci of the ultrasonic beams on the basis of the reference beam dynamically in real time.

13. The method defined in claim 8, wherein all of the ultrasonic beams are at the same ultrasonic frequency.

14. The prosthesis defined in claim 1, wherein the ultrasonic beams are all at the same ultrasonic frequency.

* * * * *